United States Patent
Brock-Fisher

(10) Patent No.: US 10,828,671 B2
(45) Date of Patent: Nov. 10, 2020

(54) INTEGRATED CIRCUIT ARRANGEMENT FOR A HEXAGONAL CMUT ULTRASOUND TRANSDUCER ARRAY WITH OFFSET COLUMNS

(71) Applicant: KONINKLIJKE PHILIPS N.V., Eindhoven (NL)

(72) Inventor: George Anthony Brock-Fisher, Andover, MA (US)

(73) Assignee: Koninklijke Philips N.V., Eindhoven (NL)

(\*) Notice: Subject to any disclaimer, the term of this patent is extended or adjusted under 35 U.S.C. 154(b) by 919 days.

(21) Appl. No.: 14/898,844

(22) PCT Filed: Jun. 24, 2014

(86) PCT No.: PCT/IB2014/062559
§ 371 (c)(1),
(2) Date: Dec. 16, 2015

(87) PCT Pub. No.: WO2014/207654
PCT Pub. Date: Dec. 31, 2014

(65) Prior Publication Data
US 2016/0136686 A1 May 19, 2016

Related U.S. Application Data

(60) Provisional application No. 61/839,641, filed on Jun. 26, 2013.

(51) Int. Cl.
*B06B 1/02* (2006.01)
*A61B 8/00* (2006.01)

(52) U.S. Cl.
CPC .......... *B06B 1/0207* (2013.01); *A61B 8/4483* (2013.01); *B06B 1/0292* (2013.01)

(58) Field of Classification Search
CPC .... B06B 1/0207; B06B 1/0292; A61B 8/4483
See application file for complete search history.

(56) References Cited

U.S. PATENT DOCUMENTS

2005/0057284 A1\* 3/2005 Wodnicki ................. A61B 8/13
327/100
2005/0094490 A1 5/2005 Thomenius et al.
(Continued)

*Primary Examiner* — Serkan Akar

(57) ABSTRACT

The present invention relates to an integrated circuit arrangement comprising: —a plurality of capacitive micromachined ultrasound transducer (CMUT) cells (40) arranged in a hexagonal array, wherein said hexagonal array comprises a plurality of alternating even and odd columns (56, 56') of CMUT cells (40) being parallel to a column direction (y), wherein the odd columns (56') are arranged offset to the even columns (56) by one-half of a dimension of a CMUT cell (40) in said column direction (y), —an application-specific integrated circuit (ASIC) (52) comprising a plurality of transmit-receive (TR) cells (54), wherein each CMUT cell (40) overlays a respective TR cell (54) in a one-to-one correspondence, wherein the ASIC (52) further comprises an offset regulator (60) for providing different beamforming delays to even and odd columns (56, 56') of the hexagonal array of CMUT cells (40) to account for the offset in the column direction (y).

11 Claims, 4 Drawing Sheets

(56) References Cited

U.S. PATENT DOCUMENTS

| | | |
|---|---|---|
| 2005/0096546 A1 | 5/2005 | Hazard et al. |
| 2005/0148132 A1 | 7/2005 | Wodnicki |
| 2009/0016163 A1 | 1/2009 | Freeman et al. |
| 2009/0182229 A1 | 7/2009 | Wodnicki |
| 2010/0298713 A1* | 11/2010 | Robinson ............. A61B 8/4483 600/459 |
| 2012/0010538 A1* | 1/2012 | Dirksen ................... A61B 8/00 601/2 |
| 2013/0128702 A1 | 5/2013 | Degertekin et al. |
| 2014/0005521 A1* | 1/2014 | Kohler ................... A61B 5/064 600/411 |
| 2015/0313575 A1* | 11/2015 | Tanaka ................. A61B 8/4494 600/447 |

* cited by examiner

INTEGRATED CIRCUIT ARRANGEMENT FOR A HEXAGONAL CMUT ULTRASOUND TRANSDUCER ARRAY WITH OFFSET COLUMNS

This application is the U.S. National Phase application under 35 U.S.C. § 371 of International Application No. PCT/IB2014/062559, filed on Jun. 24, 2014, which claims the benefit of U.S. Application No. 61/839,641 filed on Jun. 26, 2013. These applications are hereby incorporated by reference herein.

FIELD OF THE INVENTION

The present invention relates to an integrated circuit arrangement for an ultrasound transducer array. In particular, the present invention relates to an integrated circuit arrangement that comprises a set of capacitive micromachined ultrasound transducers (CMUT). The present invention further relates to an ultrasound transducer comprising such an integrated circuit as well as to an ultrasound imaging system with this ultrasound transducer.

BACKGROUND OF THE INVENTION

The heart of any ultrasound imaging system is the transducer which converts electrical energy into acoustic energy and vice versa. Traditionally, these transducers are made from piezo-electric crystals arranged in linear (1D) transducer arrays, and operating at frequencies up to 10 MHz. However, the trend towards matrix (2D) transducer arrays and the drive towards miniaturization to integrate ultrasound imaging functionality into catheters and guide wires has resulted in the development of so-called capacitive micromachined ultrasound transducers (CMUT). A CMUT comprises a membrane (or diaphragm), a cavity underneath the membrane, and electrodes forming a capacitor. For receiving ultrasound waves, ultrasound waves cause the membrane to move or vibrate, wherein the variation in capacitance between the electrodes can be detected. Thereby, the ultrasound waves are transformed into a corresponding electrical signal. Conversely, an electrical signal applied to the electrodes cause the membrane to move or vibrate and thereby transmitting ultrasound waves.

Currently CMUTs are being investigated for use in medical diagnostic and therapeutic ultrasound. Of particular interest is the integration of CMUTs and application-specific integrated circuitry (ASIC), as it is feasible to directly fabricate CMUTs on the surface of an ASIC to provide complete transducer functionality through a monolithic all-silicon process.

Furthermore, it is advantageous to fill the available area of such a device as completely as possible with active CMUTs. This results in the best overall performance. Devices have been fabricated with square as well as hexagonal patterns of CMUTs, in which the CMUTs themselves are circular or hexagonal. From the point of view of optimal filling of area with CMUTs, the hexagonal pattern is the most efficient. Typical cell dimensions of such hexagonal CMUT cells are 25-50 microns from flat edge to flat edge on the hexagon.

US 2005/0148132 A1 discloses an example of such a hexagonal pattern of CMUT cells. The therein provided integrated circuit comprises a substrate comprising a hexagonal arrangement of CMOS cells, wherein every other column of said CMOS cells is offset from adjoining columns by a distance equal to one-half of the cell dimension in said column direction, and the width of each cell is selected such that the CMOS cells line up with respective micromachined elements. A hexagonal arrangement of CMUT cells overlays the substrate, wherein the CMUT and the CMOS cells are arranged in a one-to-one correspondence.

US 2005/0148132 A1 mainly refers to the fabrication of such a micromachined hexagonal array of CMUT cells on top of a substrate. It is however silent about the way beamforming is carried out on such a hexagonal array. There is therefore still room for improvement. An interesting implementation of the integration of CMUTs and ASIC circuitry is in the case where the ASIC performs part or all of the acoustic beamforming function. Specifically, the ASIC includes circuits to perform the functions of transmit, receive, delay and summation. What is needed is a way to implement a hexagonal pattern of CMUTs with an efficient ASIC layout suitable for a microbeamformer.

SUMMARY OF THE INVENTION

It is an object of the present invention to provide an improved integrated circuit arrangement, particularly for an ultrasound transducer, that allows to implement a hexagonal pattern of CMUTs with an efficient ASIC layout suitable for a microbeamformer. Particularly, it is an object of the present invention to provide an intelligent design of such an integrated circuit arrangement that enables easy and efficient microbeamforming in such a hexagonal array of CMUTs.

In a first aspect of the present invention, an integrated circuit arrangement is presented, said integrated circuit arrangement comprising:

a plurality of capacitive micromachined ultrasound transducer (CMUT) cells arranged in a hexagonal array, wherein said hexagonal array comprises a plurality of alternating even and odd columns of CMUT cells being parallel to a column direction, wherein the odd columns are arranged offset to the even columns by one-half of a dimension of a CMUT cell in said column direction, an application-specific integrated circuit (ASIC) comprising a plurality of transmit-receive (TR) cells, wherein each CMUT cell overlays a respective TR cell in a one-to-one correspondence, wherein the ASIC further comprises an offset regulator for providing different beamforming delays to even and odd columns of the hexagonal array of CMUT cells to account for the offset in the column direction.

In a further aspect of the present invention an ultrasound transducer is presented that comprises such an integrated circuit arrangement.

In a still further aspect of the present invention, an ultrasound imaging system is presented that comprises an ultrasound transducer of this kind.

Preferred embodiments of the invention are defined in the dependent claims. It shall be understood that the claimed ultrasound transducer and the claimed ultrasound imaging system have similar and/or identical preferred embodiments as the claimed integrated circuit arrangement and as defined in the dependent claims.

In a hexagonal array of CMUTs the array can be viewed as the superposition of two rectangular arrays, with the location of alternate columns of CMUTs offset by one-half the vertical dimension (herein denoted as dimension in the column direction). In a microbeamforming ASIC, the ASIC contains circuitry under each CMUT cell that performs partial beamforming, i.e. delay and summing functions. In a hexagonal configuration, the vertical dependent delay function (delay function dependent on the position in column direction) should be different for alternating columns, due to the half-pitch vertical offset. Without this adaptation the image quality would be affected and the resulting image could be at least partially blurred.

One of the central aspects of the present invention is the accommodation of the geometrical offset between alternate columns in the hexagonal array of CMUT cells within the beamforming control. The presented beamforming control aggregates the even and odd columns, meaning that even and odd columns are preferably controlled separately. In other words, beamforming of even columns is preferably handled separately from the beamforming of the odd columns. This is realized by an intelligent hardware design on the ASIC, which is herein in general denoted as offset regulator that is configured to provide different beamforming delays to even and odd columns of the hexagonal array of CMUT cells to account for the offset in the column direction (vertical direction) between alternate columns.

The offset regulator therefore eliminates the natural geometrical offset of alternate columns in a hexagonal arrangement. Since this offset regulation is preferably hardware-implemented, the dynamic beamforming control, which is dependent on the position of each CMUT cell within the transducer array and on the desired steering angle of the resulting beam, may be realized in a "regular" manner, as if the CMUT cells were realized as rectangular or quadratic cells in an evenly distributed array without geometrical offsets between alternate columns or rows.

Separately handling the beamforming of even and odd columns furthermore has the advantage that standard components may be used for providing the beamforming delays to the even columns, and also standard components can be used for providing the beamforming delays to the odd columns. This extremely simplifies the fabrication and therefore saves production costs. Apart from that, it allows to save space on the ASIC which is left over for the CMUT and the TR cells. This again means that image resolution can be improved. In other words, area utilization of the surface is maximized for CMUT coverage.

According to a preferred embodiment, the offset regulator comprises two separate hardware units, a first hardware unit for controlling the beamforming delays of the TR cells of the even columns and a second hardware unit for controlling the beamforming delays of the TR cells of the odd columns.

Due to the hardware-implemented elimination of the geometrical offset between even and odd columns, these hardware units may be standard components that are usually used for rectangular transducer arrays (with no geometrical offset). Such a solution, of course, saves costs for the components and therefore also over all production costs.

In other words, the preferred embodiment for a microbeamformer having a hexagonal arrangement of CMUTs is to provide two copies of equal hardware units which are responsible for providing the vertical dependent delay functions (that depend on the vertical steering angle in the column direction) to the cells.

Preferably, the beamforming delays provided by the first hardware unit and the beamforming delays provided by the second hardware unit at least differ in a time-constant delay function that depends on the geometrical offset between the even and the odd columns in the column direction. The dynamic beamforming delays that are used to steer the beam into a given direction may however be the same and only vary as a function of the vertical steering angle (in the column direction).

According to a further preferred embodiment, the first hardware unit comprises a first set of buses, and the second hardware unit comprises a second set of buses. In other words, the delay functions used for microbeamforming are communicated on two separate sets of buses which run horizontally, i.e. transverse or perpendicular to the column direction, across the ASIC. The first set of buses is used to control the TR cells of the even numbered columns, and the second set of buses is used to control the TR cells of the odd numbered columns.

The first set of buses is preferably connected to the TR cells of the even columns but unconnected to the TR cells of the odd columns, and the second set of buses is connected to the TR cells of the odd columns but unconnected to the TR cells of the even columns. However, it shall be noted that this only refers to the direct connections. It is generally conceivable that the first set of buses is at least connected to the TR cells of the odd columns in an indirect manner. Similarly, the second set of buses may also be connected to the TR cells of the even columns in an indirect manner.

According to a further embodiment, the TR cells have a rectangular shape. Even though TR cells of hexagonal shape could be aligned with the hexagonal CMUT cells in an easier manner, such microbeamformer TR cells are preferably designed on a rectangular grid, as this facilitates both the design of the ASIC as well as the sawing of the crystal material into individual elements on top of the ASIC. This again saves production costs.

Despite the geometrical differences of the CMUT cells and the TR cells, it is still possible to accomplish a one-to-one correspondence, meaning that each CMUT cell is assigned to a single TR cell on the ASIC. The CMUT cells are laid out on top of the rectangular array of microbeamformer TR cells. By adjusting the basic dimensions of the CMUTs and the rectangular period spacing of the ASIC TR cells, it is possible to achieve the one-to-one correspondence between the CMUT cells and the TR cells, such that interconnections can be readily made. The interconnections can still be designed as short as possible.

In a further preferred embodiment, the TR cells are arranged in parallel rows running transverse to the column direction, wherein the TR cells in each row are arranged in line with each other.

This means that the TR cells that are assigned to CMUT cells in even columns may be arranged directly below the respective CMUT cells (having the same geometrical center), whereas the TR cells that are connected to CMUT cells in odd columns are arranged slightly offset of the respective CMUT cells. Nevertheless, the interconnections between these TR cells and the CMUT cells in odd columns can still be kept quite short.

In a further embodiment, a dimension of the TR cells in the column direction (vertical dimension) is smaller than the dimension of a CMUT cell in the column direction (vertical direction).

Thus, there is space left on the ASIC in between the TR cell rows. This extra space may be used for the arrangement of the communication lines of the microbeamforming control.

According to a preferred embodiment, the first and the second set of buses each comprise several horizontal bus lines which are arranged in the gaps between the parallel TR cell rows running transverse to the column direction. Using these gaps for the arrangement of the horizontal bus lines is a very intelligent solution, since these bus lines do then not interfere with the TR cells, while there is still enough room for the TR cells themselves.

While the foregoing discussion was mainly focusing on the horizontally arranged bus lines to account for the vertical dependent delay functions, it is clear that the horizontal dependent delay functions are preferably communicated via further bus lines that run vertically (in the column direction) across the ASIC.

According to a preferred embodiment, the first and the second set of buses each further comprise separate vertical bus lines running in column direction for providing different beamforming delays to even and odd columns of the hexagonal array of CMUT cells to account for offsets of different CMUT cells in a direction transverse to the column direction. However, the vertical bus lines do not necessarily have to be separated in the same manner as the horizontal bus lines. The horizontal dependent delays may also be controlled by a single bus system that does not differentiate between even and odd columns.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
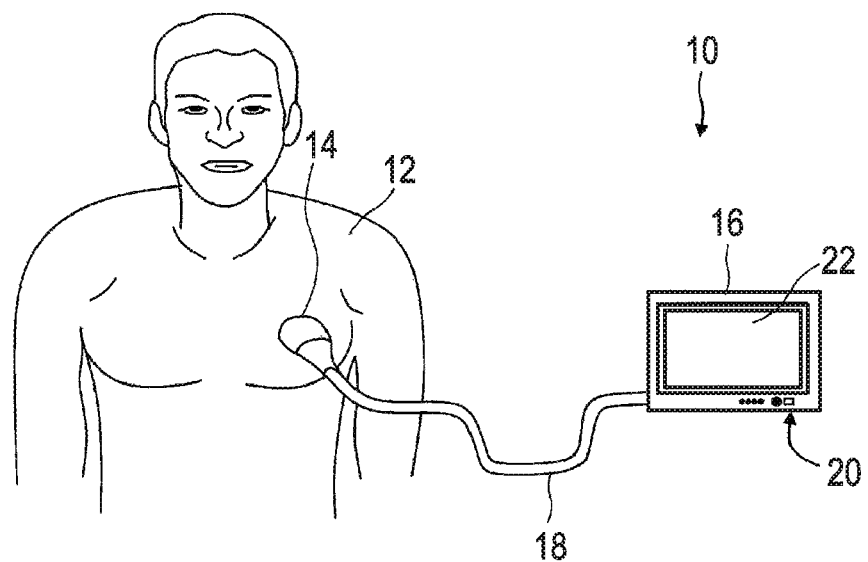
FIG. 1 shows a schematic illustration of an embodiment of an ultrasound imaging system.

FIGS. 1 and 2 illustrate the principle design of an ultrasound imaging system and the principle design of a transducer array of such an ultrasound system. These figures are used to explain the background and the working principle of ultrasound imaging. It shall be understood that the claimed integrated circuit arrangement, the claimed ultrasound transducer as well as the claimed ultrasound imaging system are not restricted to such kind of systems.

The ultrasound imaging system in FIG. 1 is generally denoted with reference numeral 10. The ultrasound imaging system 10 is used for scanning an area or volume of the body, e.g. of a patient 12. It is to be understood that the ultrasound system 10 may also be used for scanning other areas or volumes, e.g. body parts of animals or other living beings.

For scanning the patient 12, an ultrasound probe 14 may be provided. In the embodiment shown, the ultrasound probe 14 is connected to a console device 16. The console device 16 is shown in FIG. 1 as a mobile console. This console 16 may, however, also be realized as a stationary device. The console device 16 is connected to the probe 14 via an interface 18 formed in a wired manner. Further, it is contemplated that the console device 16 may also be connected to the probe 14 in a wireless manner, for example using UWB transmission technology. The console device 16 may further comprise an input device 20. The input device 20 may have buttons, a key pad and/or a touchscreen to provide an input mechanism to a user of the ultrasound imaging system 10. Additionally or alternatively, other mechanisms may be present in the input device 20 to enable a user to control the ultrasound imaging system 10.

Further, the console device 16 comprises a display 22 to display display data generated by the ultrasound imaging system 10 to the user. By this, the volume within the patient 12 that is scanned via the ultrasound probe 14 can be viewed on the console device 16 by the user of the ultrasound system 10.

Figure 2A:
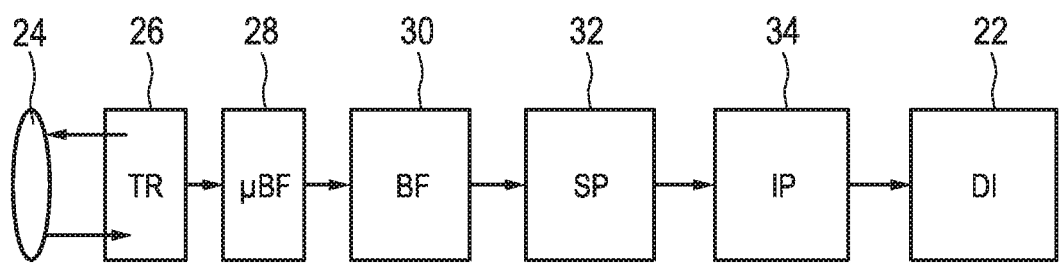
FIG. 2a shows a block diagram that schematically illustrates the processing of signals and data in an ultrasound imaging system.

FIG. 2a shows a block diagram illustrating the typical operations of a 2D or 3D ultrasound imaging system 10. An ultrasound transducer 26 emits ultrasound signals which generate a response from the volume 24 back to the transducer 26. The received signals from the volume 24 are transformed by the transducer 26 into electrical signals. These electrical signals will then be beamformed by several microbeamformers 28 and finally by a main or master beamformer 30, as this will be explained in more detail below. The main beamformer 30 provides an image signal to a signal processor 32. The signal processor 32 in turn generates detected acoustic data—the so-called image data—therefrom. An image processor 34 converts the image data into display data to be displayed on the display 22. The image processor 34 may prepare 2D tomographic slices of the volume 24 to be displayed or may convert or render the image data into a 3D image that is displayed on the display 22.

Figure 2B:
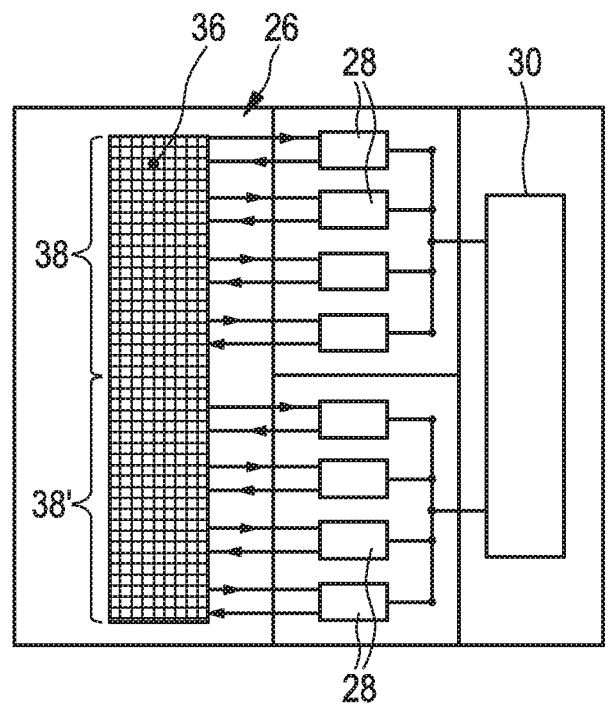
FIG. 2b shows an example of a schematic detailed view on a transducer array and a beamformer.

FIG. 2b is a schematic detailed view of the transducer array 26, the microbeamformers 28 and the main beamformer 30. The transducer array 26 is usually formed of a plurality of acoustic elements, which are herein denoted as transducer elements 36. According to the present invention, these transducer elements 36 are realized by capacitive micro-machined ultrasound transducer (CMUT) cells 40, which are arranged in a hexagonal matrix array, as this will be explained in more detail with reference to FIG. 3. The transducer elements 36 transmit the ultrasound signals and receive the generated responses. A transducer array 26 may comprise thousands of transducer elements 36 forming a multitude of sub-arrays 38, 38'. For illustrative purposes, merely two sub-arrays 38, 38' are shown in FIG. 2b. However, the number of sub-arrays 38, 38' may also be greater than 2, e.g. 8, 16, 32, 64, 128, etc.

The transducer array 26 may have a plurality of microbeamformers 28, which control both transmission and reception of acoustic pulses through the transducer elements 36, and combine the acoustic responses generated by the scanned medium in order to form sub-array summed acoustic signals, which are then transferred from the transducer array 26 through signal lines to the main beamformer 30. In the shown example, the two sub-arrays 38, 38' are each connected to four different microbeamformers 28. However, the number of microbeamformers 28 in each group may also be different from 4, e.g. 8, 16, 32, 64, etc. Each signal line within a sub-array 38, 38' may emanate from one microbeamformer 28 and is joint with the other signals of that sub-array 38, 38' to form a sub-array group output. The sub-array group output is then connected to the main beamformer 30 as described below.

There are two main phases of beamforming, namely transmit and receive. During transmittance, acoustic pulses are generated from the transducer elements 36 of the transducer array 26. During the receive phase, echoes from those pulses in the volume 24 are received by the acoustic elements of the transducer array 26, amplified and combined. For beamforming in the transmit phase, transmit delay pulsers generate delayed high voltage pulses. The acoustic pulses are transmitted by the transducer elements 36. The acoustic pulses are timed relative to each other to generate a focus in the three-dimensional space of the insonified medium. In the receive phase, the acoustic pulses previously transmitted are echoed by structures in the volume 24. Between the time that the acoustic pulses are transmitted and the generated pulse echoes are received by the transducer elements 36, so-called T-R (transmit/receive) switches switch to the receive position. Acoustic pulses are received by the transducer elements 36 from many points on the body, and receive samplers take periodic samples of the resulting acoustic wave to generate analog samples, which are small voltages. The analog samples are then delayed by receive delays. The receive delays may be static delays, meaning they are unchanged during the course of acoustic reception. The receive delays may also be programmed and thereby modified dynamically during the receive phase so as to maintain a constant array focus as the transmitted pulses propagate into the medium and create echoes from successively deeper locations in the medium. The separately delayed receive signals are summed together by summers, and after summing, variable gain amplifiers perform time gain compensation. Time variable gain is required because the signals received by the transducer elements 36 from later times correspond to deeper depths of the body, and are therefore attenuated. The variable gain amplifiers compensate for this attenuation by increasing output. The sub-array summed acoustic signals are transmitted by the signal lines.

Hence, the beamforming control provides dynamic and/or static beamforming to generate a plurality of sub-arrays summed acoustic signals, which are received by a further static and/or dynamic beamformer in a main beamformer 30. The main beamformer 30 performs static and/or dynamic beamforming to generate a set of fully beamformed image signals. Hence, one main or master beamformer 30 sub-groups a multitude of microbeamformers 28. By this, the number of signals from the beamformer 30 to the signal processor 32 may be significantly reduced compared to the number of transducer elements 36.

Figure 4:
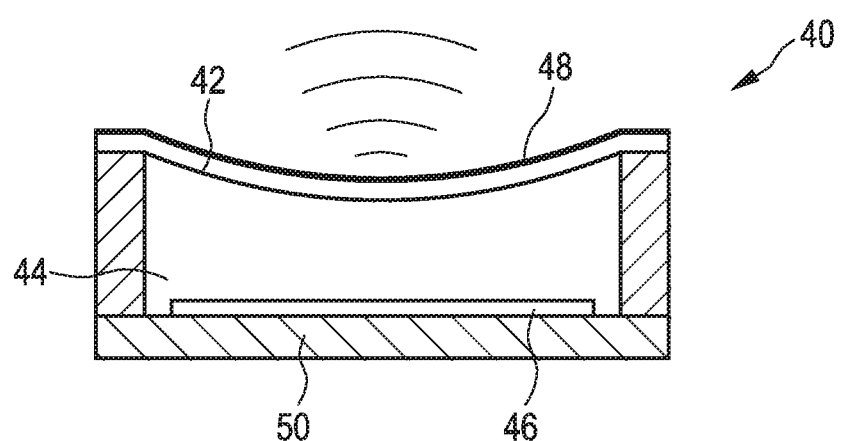
FIG. 4 schematically illustrates a cross-section of a CMUT cell to illustrate the principle design and function of such a CMUT cell.

A CMUT cell 40 that is according to the present invention preferably used as a transducer element 36 is shown in FIG. 4 in a schematic cross-section. Such a CMUT cell 40 usually comprises a membrane 42, a cavity 44 underneath the membrane 42, and electrodes 46, 48 which form a capacitor. For receiving ultrasound waves, ultrasound waves cause the membrane 42 to move or vibrate and the variation in capacitance between the electrodes 46, 48 can be detected. Thereby, the ultrasound waves are transformed into a corresponding electrical signal. Conversely, an electrical signal applied to the electrode 46, 48 causes the membrane 42 to move or vibrate and thereby transmitting ultrasound waves. The membrane 42 itself may, for example, be made of silicone nitrate. The CMUT cell 40 is preferably fabricated on a substrate 50 which may comprise heavily doped silicone. The electrodes 46, 48 are preferably made of a conductive material, such as a metal alloy. In order to guarantee elastic vibrations of the membrane 42, the cavity 44 is preferably evacuated. However, it may also be filled with any suitable gas. It shall be understood that the CMUT cells used in the integrated circuit arrangement according to the present invention may differ in its design from the CMUT cell 40 that is schematically shown in FIG. 4. FIG. 4 is herein only used for illustrative purposes and to explain the general working principle of such a CMUT cell.

Figure 3A:
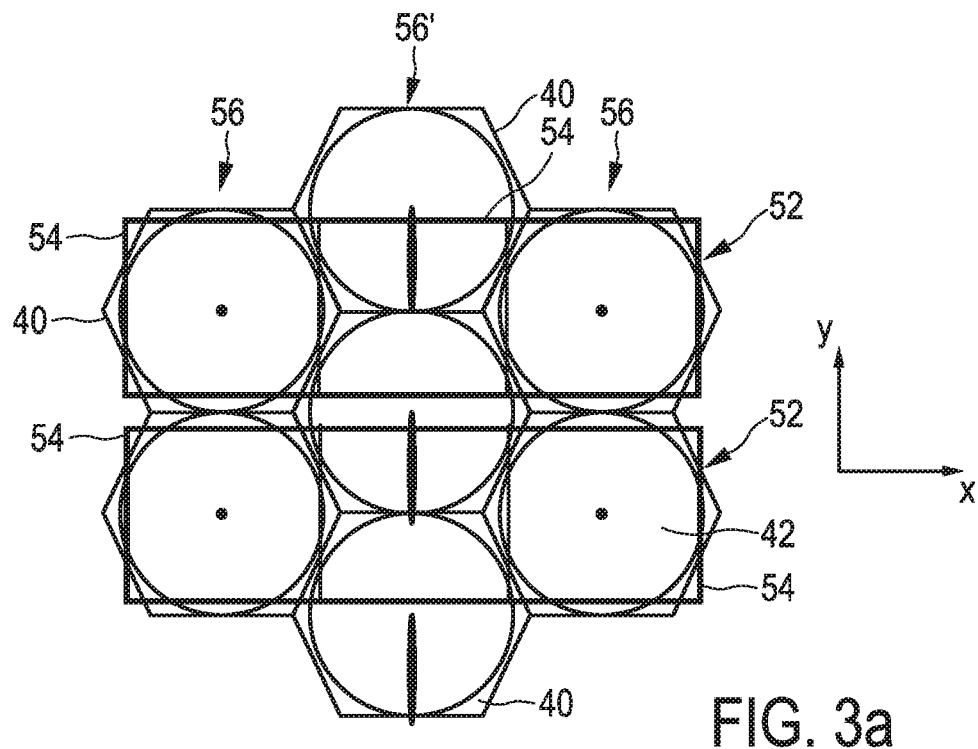
FIGS. 3a and 3b schematically show a hexagonal arrangement of CMUT cells with an efficient ASIC layout that is suitable for a microbeamformer according to an embodiment of the present invention.

FIG. 3a schematically shows a part of the integrated circuit arrangement according to the present invention. It comprises a plurality of CMUT cells 40 which are arranged in a hexagonal pattern. The hexagonal pattern of CMUT cells 40 is overlaid on top of an ASIC 52. The ASIC 52 comprises a plurality of transmit-receive (TR) cells 54. These TR cells 54 include parts or all of the microbeamforming circuitry, such that each TR cell 54 forms a part of a microbeamformer 28. Specifically, the ASIC 52 includes circuits to perform the functions of microbeamforming and/or beamforming, i.e. transmit, receive, delay, and summation. Typically, such microbeamforming TR cells 54 are designed on a rectangular grid, as this facilitates both the design of the ASIC 52 as well as the sawing of the crystal material into individual elements on top of the ASIC 52.

Each CMUT cell 40 is assigned and connected to a single TR cell 54 in a one-to-one correspondence. The CMUT cells 40 are therein arranged in a hexagonal pattern. This hexagonal pattern allows to arrange the plurality of CMUT cells 40 in a densest possible packing manner. A hexagonal arrangement as shown in FIG. 3a therefore maximizes the area utilization of the surface for CMUT coverage. If the side dimension of a CMUT cell 40 is denoted by s, the spacing between two centers of adjacent CMUT cells 40 is in any of the three major access of the hexagonal pattern only √3 s≈1.73 s. The fill factor that can be achieved with the usually circular membranes 42 in such a hexagonal pattern is around 90.6%, which follows from the following dependency:

$$A_{circular\ membrane} = \pi\left(\frac{\sqrt{3}}{2}s\right)^2 = \frac{3}{4}\pi s^2$$

$$A_{hexagonal\ cell} = \frac{3}{2}\sqrt{3}\,s^2$$

$$\text{Fill factor} = \frac{A\ circular\ membrane}{A\ hexagonal\ cell} = \frac{\pi}{2\sqrt{3}} \approx 90.6\%$$

From the point of view of optimal filling of area with CMUT cells 40, the hexagonal pattern is the most efficient. The hexagonal arrangement furthermore has the advantage that the effective acoustic pitch in the x+30° and the y-direction is reduced below the inherent hexagonal pitch spacing of the CMUTs 40 and below the y-pitch of the TR cells 54. This increases the frequency at which grating lopes become a significant source of artifacts for a given steering angle.

Figure 3B:
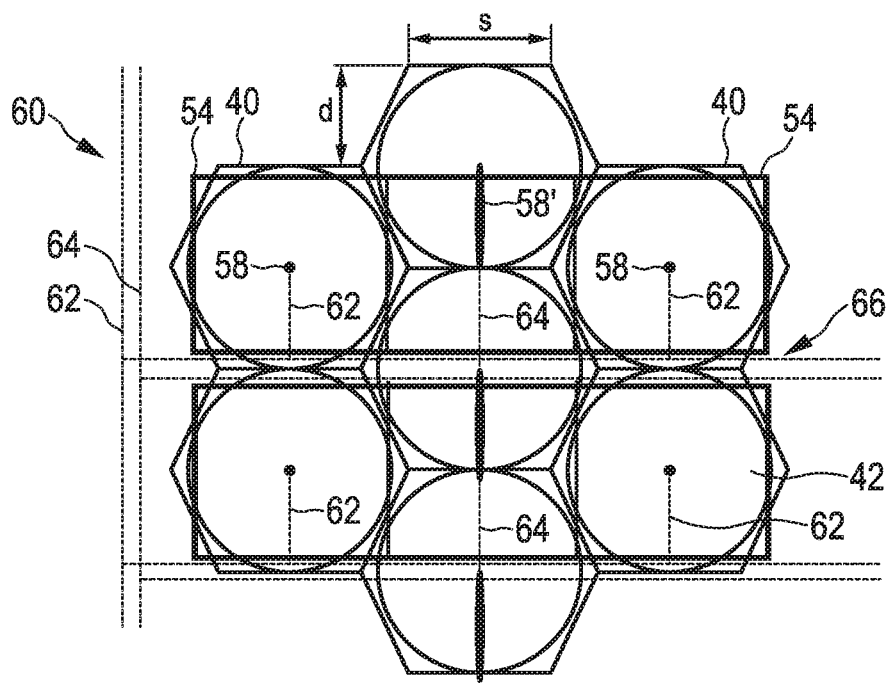

It can be further seen in FIGS. 3a and 3b that due to the hexagonal arrangement of the CMUT cells 40, they appear to be arranged in different straight columns 56, 56', wherein CMUT cells in one column 56, 56' are all aligned with each other. However, as indicated in the upper part of FIG. 3b, CMUT cells 40 of adjacent columns 56, 56' are arranged offset to each other by one-half the vertical pitch of a hexagonal CMUT cell 40. This offset is indicated in FIG. 3b by d, wherein:

$$d = \frac{\sqrt{3}}{2}s$$

In other words, the hexagonal array of CMUT cells 40 comprises a plurality of alternating even columns 56 and odd columns 56' being parallel to a column direction y, wherein the odd columns 56' are arranged offset to the even column 56 by d, seen in column direction y. Since the TR cells 54 are preferably arranged in parallel rows running in x-direction (perpendicular to the column direction y), this means that TR cells 54 which are assigned to CMUT cells 40 in odd columns 56' are also arranged slightly offset from them. Connection pads 58' that are used to connect the TR cells 54 to the CMUTs 40 are in odd columns 56' therefore slightly larger than in even columns 56 (compare reference numerals 58 and 58').

More important is however that the vertical dependent delay function (in column direction y) must be different for alternating columns, due to the half-pitch vertical offset d. This vertical dependent delay function offset varies as a function of the vertical steering angle.

According to the present invention this is solved by providing an offset regulator 60 on the ASIC 52 for providing different beamforming delays to even and odd columns 56, 56' of the hexagonal array of CMUT cells 40 in order to account for the offset d. The geometrical offset between alternate columns 56, 56' is thereby preferably eliminated by a hardware-implemented solution. The presented beamforming control aggregates the even and odd columns 56, 56', meaning that even and odd columns 56, 56' are preferably controlled separately. According to a preferred embodiment this is realized by providing two copies of the hardware which is responsible for providing the vertical dependent delay functions to the TR cells 54. These functions are communicated on two separate sets of buses 62, 64.

A first set of buses 62 is used to control even numbered columns 56 and a second set of buses 64 is used to control odd numbered columns 56'. Separately handling the beamforming of even and odd columns 56, 56' has the advantage that standard components may be used for providing the beamforming delays to the even and odd columns 56, 56' separately. If only one communication bus was used for all columns 56, 56' together, the delay values that would have to be applied to each CMUT cell 40 in the alternating columns 56, 56' would not only depend on the steering angle and the position of each CMUT cell on the array, but also the offset between alternate columns 56, 56' would have to be taken into account. In the presented solution the beamforming delays provided by the first set of buses 62 and the beamforming delays provided by the second set of buses 64 may, however, be implemented to differ in a time-constant delay function that depends on the offset d between even and odd columns 56, 56' in the column direction y. Since this static difference is thereby already accounted for, the two separate sets of buses 62, 64 may control the delays as if the CMUT cells 40 were realized as rectangular or quadratic cells in an evenly distributed array without geometrical offsets between alternate columns or rows. This extremely facilitates the microbeamforming control of the system.

Of course, the first and the second set of buses 62, 64 may also comprise separate vertical bus lines (not shown) running in column direction y for providing different beamforming delays to even and odd columns of the hexagonal array of CMUT cells 40 to account for offsets of different CMUT cells in the direction x. However, since there is a constant distance between adjacent CMUT cells 40 in x-direction, this could also be handled by only one communication bus (as usual).

A still further advantage can be seen in FIG. 3b. The vertical dimensions in y-direction of the TR cells 54 are preferably chosen to be smaller than the respective dimensions in vertical direction y of the CMUT cells 40. Therefore, a small space is left between adjacent rows of TR cells 54. This extra space can be used to place the horizontal bus lines of the first and second set of buses 62, 64 on the ASIC 52.

In summary, the present invention provides an intelligent combination of a hexagonal pattern of CMUTs with an efficient ASIC layout suitable for microbeamforming. The intelligent design of the provided integrated circuit arrangement allows easy and efficient micro beamforming with such a hexagonal array of CMUT cells. Due to the separate consideration of even and odd columns within the hexagonal cell array the micro beamforming technique accounts for the vertical offset of alternating columns of sensors in an easy and cost-efficient way.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An integrated circuit arrangement comprising:
a plurality of capacitive micromachined ultrasound transducer (CMUT) cells arranged in a hexagonal array, wherein said hexagonal array comprises a plurality of alternating even and odd columns of CMUT cells being parallel to a column direction, wherein the plurality of alternating even and odd columns occupy a same region defined by the hexagonal array, and wherein the odd columns are arranged offset to the even columns by one-half of a dimension of a CMUT cell in said column direction,
an application-specific integrated circuit (ASIC) comprising a plurality of transmit-receive (TR) cells, wherein each CMUT cell overlays a respective TR cell in a one-to-one correspondence,
wherein the ASIC further comprises an offset regulator for providing different beamforming delays to even and odd columns of the hexagonal array of CMUT cells to account for the offset in the column direction, wherein the offset regulator comprises:
a first hardware unit including a first set of busses that are connected to the TR cells of the even columns but not connected to the TR cells of the odd columns and a first beamformer for controlling the beamforming delays of the TR cells of the even columns; and
a second hardware unit including a second set of busses that are connected to the TR cells of the odd columns but not connected to the TR cells of the even columns and a second beamformer for controlling the beamforming delays of the TR cells of the odd columns;
wherein the first beamformer and the second beamformer are respectively configured to control the plurality of alternating even and odd columns of the CMUT cells as different rectangular arrays occupying the same region defined by the hexagonal array, and wherein the beamforming delays provided by the first hardware unit and the beamforming delays provided by the second hardware unit at least differ in a time-constant delay function that depends on the offset between the even and odd columns in the column direction.

2. The integrated circuit arrangement as claimed 1, wherein the TR cells have a rectangular shape.

3. The integrated circuit arrangement as claimed in claim 1, wherein the TR cells are arranged in parallel rows running transverse to the column direction, and wherein the TR cells in each row are arranged in line with each other.

4. The integrated circuit arrangement as claimed in claim 1, wherein a dimension of the TR cells in the column direction is smaller than the dimension of a CMUT cell in the column direction.

5. The integrated circuit arrangement as claimed in claim 1, wherein the first and the second set of busses each comprise separate horizontal bus lines which are arranged in gaps in between the parallel TR cell rows running transverse to the column direction.

6. The integrated circuit arrangement as claimed in claim 1, wherein the first and the second set of busses each further comprise separate vertical bus lines running in column direction for providing different beamforming delays to even and odd columns of the hexagonal array of CMUT cells to account for offsets of different CMUT cells in a direction transverse to the column direction.

7. An ultrasound transducer comprising the integrated circuit arrangement as claimed in claim 1.

8. An ultrasound imaging system comprising the ultrasound transducer as claimed in claim 7.

9. The integrated circuit arrangement as claimed in claim 1, wherein each TR cell comprises microbeamforming circuitry such that each TR cell forms part of a microbeamformer.

10. The integrated circuit arrangement as claimed in claim 1, wherein the first and second hardware units are copies of one another.

11. The integrated circuit arrangement as claimed in claim 1, wherein the beamforming delays provided by the first hardware unit and the beamforming delays provided by the second hardware unit comprise different static delays.

* * * * *